(12) United States Patent
Lamphere et al.

(10) Patent No.: US 6,824,506 B1
(45) Date of Patent: Nov. 30, 2004

(54) SHAPED DIAPHRAGM FOR A CENTRIFUGE SYSTEM ROTOR

(75) Inventors: David G. Lamphere, Framingham, MA (US); Thomas D. Headley, Wellesley, MA (US)

(73) Assignee: Haemonetics Corporation, Braintree, MA (US)

(*) Notice: Subject to any disclaimer, the term of this patent is extended or adjusted under 35 U.S.C. 154(b) by 0 days.

(21) Appl. No.: 09/733,624

(22) Filed: Dec. 8, 2000

(51) Int. Cl.⁷ ................................................ B04B 11/00
(52) U.S. Cl. ........................... 494/41; 494/45; 494/48; 92/98 R; 92/104
(58) Field of Search ........................... 494/41, 45, 47, 494/48; 210/224–231; 92/96–104

(56) References Cited

U.S. PATENT DOCUMENTS

| | | | |
|---|---|---|---|
| 1,885,457 A | * | 11/1932 | Lord et al. |
| 2,179,807 A | * | 11/1939 | Asmussen |
| 2,661,150 A | | 12/1953 | Abbott, Jr. |
| 3,096,283 A | * | 7/1963 | Hein |
| 3,244,362 A | * | 4/1966 | Hein |
| 3,244,363 A | | 4/1966 | Hein |
| 3,297,244 A | * | 1/1967 | Hein |
| 3,456,875 A | * | 7/1969 | Hein |
| 4,077,882 A | | 3/1978 | Gangemi ..................... 210/90 |
| 4,608,164 A | * | 8/1986 | Neu |
| 5,733,253 A | | 3/1998 | Headley et al. |
| 5,885,239 A | * | 3/1999 | Headley et al. |
| 6,074,335 A | | 6/2000 | Headley et al. ............... 494/26 |

OTHER PUBLICATIONS

International Search Report; PCT/US01/48272, Dec. 7, 2001.

* cited by examiner

*Primary Examiner*—David Sorkin
(74) *Attorney, Agent, or Firm*—Bromberg & Sunstein LLP (57) ABSTRACT

A shaped diaphragm as a part of a fluid processing disposable set acting as a centrifuge system rotor. The fluid processing disposable set has a variable-volume chamber and a fluid port. The shaped diaphragm defines a wall of the variable-volume chamber. The chamber is in fluid communication with the fluid port and is defined by a fixed wall and an elastic wall. The elastic wall is formed by the shaped diaphragm. The disposable set may also have a rotary seal coupled to the fluid port and fluidly coupled to the variable-volume chamber. The shaped diaphragm may be convoluted. The convolution may be a single fold and may have a plurality of folds located symmetrically about an axis. The shaped diaphragm may, alternatively, be essentially planar in an unstretched position while varying in thickness along a diaphragm dimension. Centrifuge rotors, systems, and methods for selective harvest of fluid constituents from a whole fluid are detailed.

24 Claims, 8 Drawing Sheets

FIG. 10a

US 6,824,506 B1

SHAPED DIAPHRAGM FOR A CENTRIFUGE SYSTEM ROTOR

TECHNICAL FIELD

This invention relates to centrifuge systems for the general processing of fluids and, more specifically, the separation of such fluid into its constituents.

BACKGROUND ART

Centrifugal fluid-processing systems have been in existence for some time. A particularly common use for such systems is for the processing and separation of whole blood into red blood cell, white blood cell, plasma, platelet and other constituents or components. Such centrifuge systems are generally categorized as either being continuous-flow devices or discontinuous-flow devices.

In continuous-flow systems, whole fluid is input through a conduit into a spinning rotor where the fluid is separated into its components. A component of interest may be collected and any unwanted components may be removed through a second conduit on a continuous basis while more whole fluid is being input. These systems typically employ a belt-type rotor which has a relatively large diameter but a relatively small (typically 100 ml or less) processing volume. Although continuous-flow systems have an advantage that the total amount of fluid being processed may be relatively small, they have the disadvantage that the diameter of the rotor is large. Therefore, such systems are large and also tend to be complicated to set up and use.

In discontinuous-flow systems, whole fluid is also input through a conduit into a rotor where component separation takes place. These systems usually employ a bowltype rotor having a relatively large (typically 200 ml or more) volume that must be essentially filled with fluid before any of the desired components can be harvested. When the bowl is full, the input of fresh fluid is stopped and the unwanted components are removed through the same conduit. When the rotor has been emptied, new whole fluid is introduced and a second cycle begins. This process continues until a required amount of component has been collected. Thus, removal occurs intermittently in batches rather than on a continuous basis. Discontinuous-flow systems have an advantage that their rotors are relatively small in diameter but have the disadvantage that the total volume of fluid being processed is large.

Centrifuge systems and methods for processing blood and other fluids that are compact and easy to use and that do not have the disadvantages of prior-art discontinuous-flow systems have been previously disclosed in a number of U.S. patents assigned to Transfusion Technologies Corporation. Such systems generally include a disposable set that acts as a centrifuge rotor. In particular, U.S. Pat. No. 6,074,335, entitled "Rotor with Elastic Diaphragm Defining a Liquid Separating Chamber of Varying Volume," issued on Jun. 13, 2000, as well as its parent, U.S. Pat. No. 5,733,253, issued on Mar. 31, 1998, are hereby incorporated herein by reference. Embodiments of this rotor include an elastic, impermeable wall (elastic diaphragm) which defines at least a portion of a variable-volume fluid processing chamber. Rotor embodiments include a rigid mounting member to which the elastic diaphragm is mounted and which is held onto and spun by a chuck. This rigid mounting member may include a rigid wall which, together with the elastic diaphragm, defines the variable-volume chamber. Both the diaphragm and the rigid wall are referred to as chamber boundaries since each of them define portions of the interior of the variable-volume processing chamber with each having one side which does not come into contact with the biological fluid. In some embodiments, the diaphragm may be located inside other walls on the exterior of the rotor, such as the rigid boundary wall or an exterior shell.

Numerous rotor embodiments are disclosed in U.S. Pat. No. 6,074,335. By way of example, the rigid boundary wall may be large enough to surround the maximum volume that may be taken up by the chamber, or the rigid mounting member may be only large enough to provide a place where the diaphragm may be mounted and where a chuck can hold and spin the rotor. In another rotor embodiment, the rigid boundary wall is a substantially imperforate circular wall which extends to the periphery of the processing chamber, so as to define the top of the processing chamber. The elastic diaphragm is attached to the perimeter of the wall and defines the remainder of the processing chamber. In yet another embodiment, the rigid boundary wall is substantially imperforate but defines one opening near the rotor's axis of rotation permitting a conduit to pass therethrough so as to be in fluid communication with the processing chamber. In alternative embodiments, the rigid boundary wall may have a plurality of openings and, possibly, numerous conduits for controlling the flow into and/or out of the rotor while the rotor is being spun. Some rotors feature a fixed portion that does not rotate during centrifugation. In particular, such a fixed rotor portion may provide a fluid conduit or, perhaps, more than one such conduit, affording fluid communication between an input source of whole fluid, the rotating portion of the rotor, and an output. Rotors having a fixed portion may include a rotary seal. Embodiments of rotary seals are disclosed in both U.S. Pat. Nos. 6,074,335 and 5,904,355, the latter reference hereby incorporated herein by reference.

Figure 1:
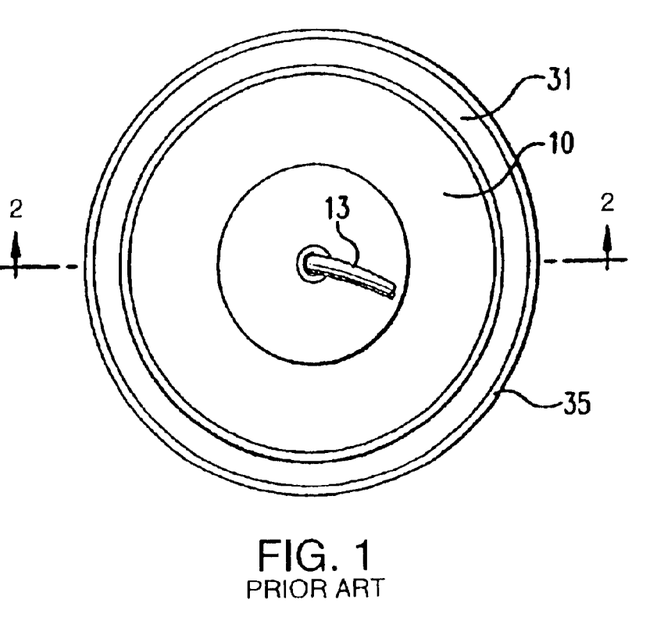
FIG. 1 is a top plan view of a prior art rotor embodiment.
Figure 2:
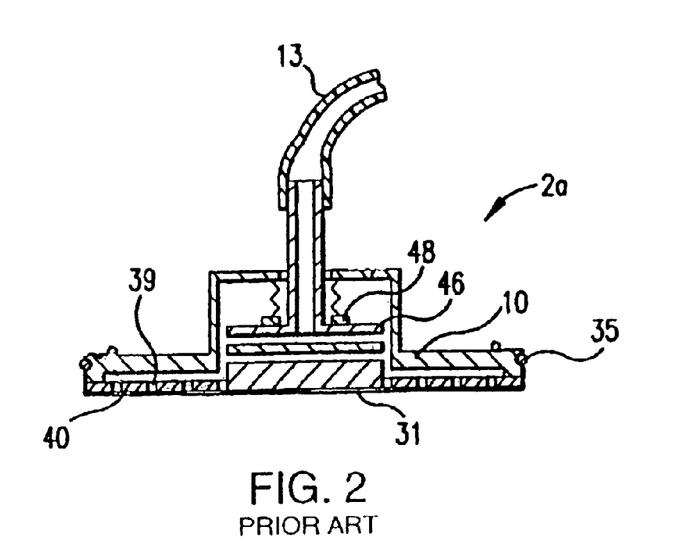
FIG. 2 shows a cross-section of the rotor embodiment illustrated in FIG. 1.

FIG. 1 is a top plan view of a prior art rotor embodiment, while FIG. 2 shows a cross-section of the rotor embodiment illustrated in FIG. 1. Rotor 2a has an elastic boundary (i.e., an impermeable diaphragm 31) sealed to a rigid, imperforate boundary wall 10 by an O-ring 35 or other means. Diaphragm 31 is preferably made of an elastic, stretchable and resilient material, such as latex or silicone rubber. Diaphragm 31 is a simple diaphragm as shown because, as is hereby defined, in its unstretched condition, it exhibits an essentially constant thickness and is essentially planar. It is to be understood that a simple diaphragm 31 may include a non-planar region in the immediate vicinity of its attachment to (or its seal with) wall 10 (i.e. a rim for mounting or other such equivalently functional mounting feature). A perforate interior wall 40—also referred to as a plate—having holes 39, is attached under the rigid boundary wall 10. Preferably, the boundary wall 10 and the interior wall 40 are made out of a rigid thermoplastic. The perforate interior plate 40 is held a short distance away from the imperforate boundary wall 10 by standoffs (not shown), thereby forming a passage 44.

Figure 3:
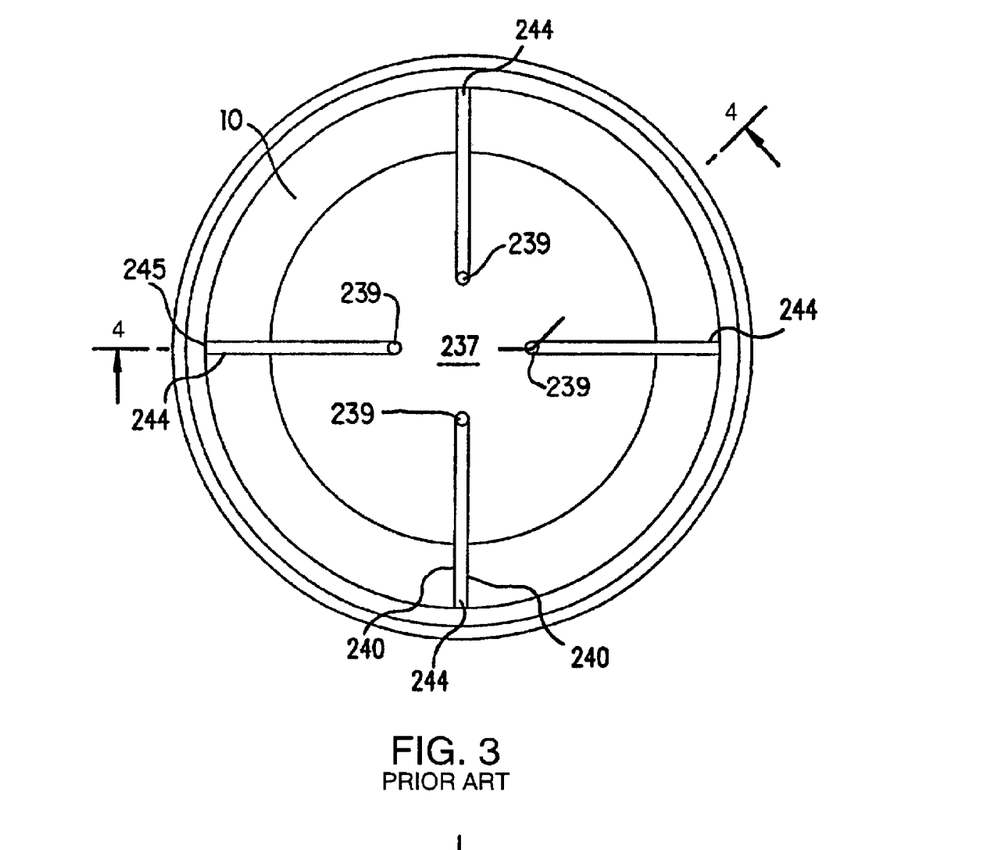
FIG. 3 is a bottom view of another prior art rotor embodiment shown without its simple diaphragm 31.
Figure 4:
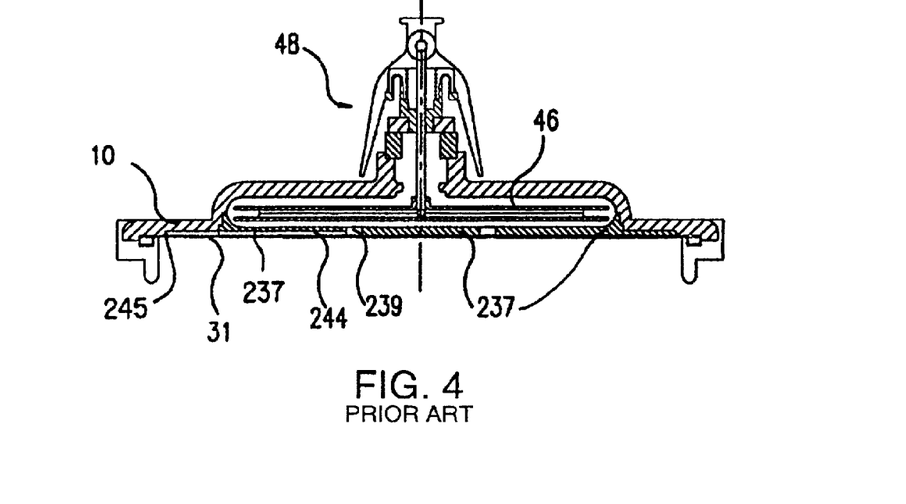
FIG. 4 is a cross-section of the rotor embodiment of FIG. 3

FIG. 3 is a bottom view of another prior art rotor embodiment illustrated without a diaphragm 31 in place. FIG. 4 is a cross-section of the rotor of FIG. 3. The embodiment of FIGS. 3 and 4 illustrate a different type of fluid outlet control from the previous configuration. This rotor embodiment features grooves 244, that are preferably radially aligned, formed on the bottom of boundary wall 10 as the outlet control means, instead of tubes or an interior perforate wall/plate 40. The grooves 244 are defined by vertical channel walls 240 provided by boundary wall 10; if the vertical channel walls 240 are placed close enough to each other so that diaphragm 31 will not block off grooves 244 under pressurized or static conditions, they can keep channels (the grooves 244) open from the holes 239, which connect the processing chamber 30 and the collector assembly 46, to, if desired, the periphery of the rotor, or to whatever radius (the radius is illustrated generically in FIGS. 3 and 4 as reference item 245) it is desired to maintain a channel. The FIG. 4 rotor has a fixed portion (including the collector assembly 46) which interfaces with the rotating portion of the rotor at a rotary seal 48. An internal wall 237, shown in FIGS. 3 and 4 as a portion of boundary wall 10, is necessary to keep the spinning diaphragm 31 from coming into contact with the fixed portion and possibly being abraded leading to premature failure.

Figure 5:
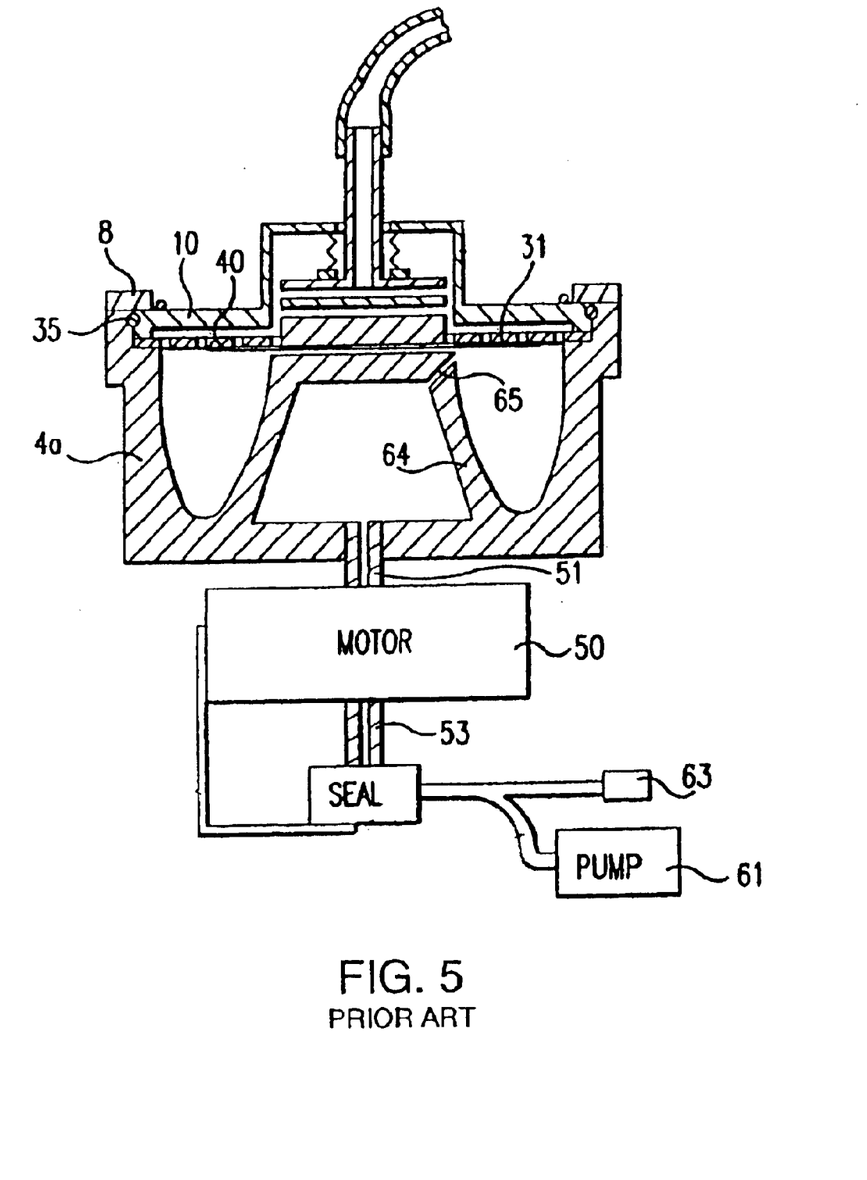
FIG. 5 illustrates, in cross-section, a prior art centrifuge system incorporating, by example only, the rotor embodiment of FIG. 1
Figure 6:
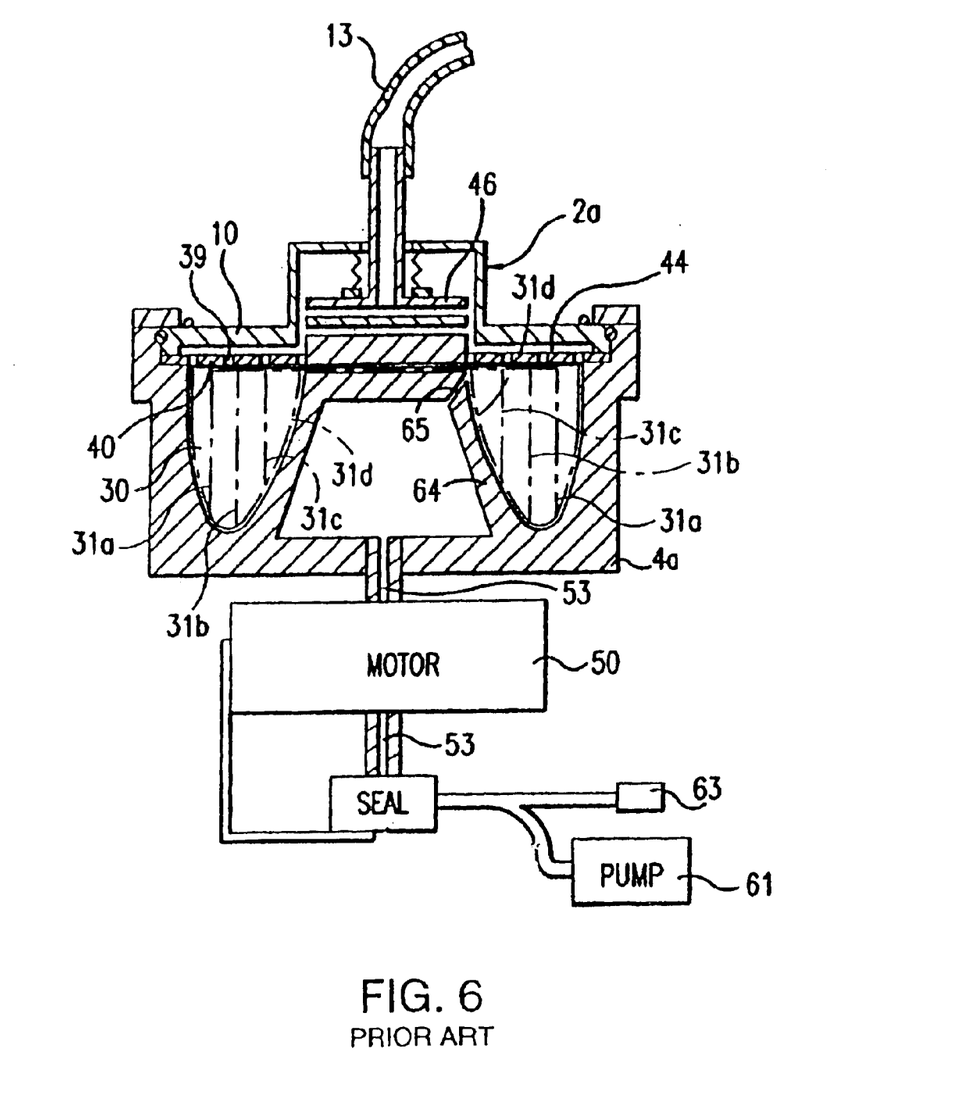
FIG. 6 depicts the prior art system of FIG. 5, further indicating, by items 31a–d, sequential changes in the volume of processing chamber 30.

Referring now to FIGS. 5 and 6 (showing a system incorporating, by example only, the rotor embodiment of FIG. 1), rotor 2a may be spun in a centrifuge system that includes a chuck 4a, for holding (with clamp 8 and sealing O-ring 35) and spinning the rotor 2a, and a pressurized fluid supply for supplying a pressurized control fluid (preferably, a gas) adjacent the rotor's diaphragm 31 (in this embodiment, out of hole 65 in chuck 4a, gas pumped through channel 53 by pump 61), while the rotor 2a is being spun by motor 50 and shaft 51. The pressurized gas may be used to force fluid out of the rotor's processing chamber 30. The system may also include means for applying a vacuum to the exterior side of the diaphragm 31 (i.e., the side that does not come into contact with the fluid being processed), so as to draw fluid into the processing chamber 30. The chuck, generally, has an outer peripheral wall extending from a rotatable base so as to define a cylindrical cavity into which the rotor's diaphragm may expand. Simple diaphragm 31 is mounted along the bottom of interior wall 40. In the chuck embodiment of FIG. 5, chuck 4a also has, extending from its base, a core 64, so that chuck 4a defines an annular cavity into which simple diaphragm 31 may expand and from which it may contract, thereby accepting and releasing fluid. FIG. 6 shows the rotor 2a (FIG. 1 embodiment shown, although use of FIG. 4 embodiment would be functionally equivalent) while it is spinning and while whole fluid flows into the rotor 2a from the rest of a disposable set. The disposable set includes, but is not limited to, tube 13, boundary wall 10, and collector assembly 46. While rotor 2a is spun by chuck 4a, the collector assembly 46, including the conduit connected to tube 13, is held in place by a brace (not shown). When fluid touches either boundary wall 10 or interior plate 40, it is propelled by centrifugal force towards the periphery of rotor 2a. As more fluid enters, it continues to be propelled to the perimeter eventually flowing through the holes in the interior plate 40. Alternatively, in the case of the rotor of FIGS. 3 and 4, fluid would flow toward the periphery via holes 239 and channels 244. As the volume of the fluid and the processing chamber 30 increases, simple diaphragm 31 stretches to allow the fluid to reach the furthest diameter and, at some point in the process, takes on a shape shown by line 31a. As fluid enters the rotor, displaced air in the chuck 4a escapes through hole 65, down the shaft hole 53 and out of exhaust valve 63. If necessary, the fluid flow rate may be increased by a vacuum in the chuck 4a generated by the pump 61 or a separate vacuum supply (such as a separate vacuum pump or a centralized, institutional vacuum provided through a vacuum line). As more and more fluid enters rotor 2a, the diaphragm 31 changes shape to accommodate it. As it is filled further, simple diaphragm 31 sequentially takes on the shapes shown by line 31b and line 31c and finally, when the rotor 2a is full, takes on the shape of the annular cavity of chuck 4a, as shown by line 31d. As diaphragm 31 stretches to accommodate the expanding size of the processing chamber 30, it comes into contact with the annular chuck cavity in a sequential manner. As successive portions of diaphragm 31 come into contact with the cavity, those portions may become immobilized and cease to stretch, while other portions of diaphragm 31 that have not yet come into contact with the chuck continue to stretch. This sequence of events clearly demonstrates that processing chamber 30 is truly a variable-volume chamber.

Chuck 4a may be shaped so as to minimize variations in the amount of stretching between different portions of the diaphragm. The inherently non-uniform loading/stretching of simple diaphragm 31 could, potentially, reduce its useful life.

Further, the prior art embodiments of chuck 4a have centrosymmetric features. In other words, the annular cavity (cavities) which the elastic diaphragm 31 is capable of expanding into, upon the filling of the resultant fluid processing chamber 30, and contracting out from, upon the emptying of chamber 30, are symmetrically provided about the axis of rotation of the centrifuge system. Thus, filling with whole fluid and harvesting of fluid constituents take place essentially evenly as measured from a given radial distance away from the axis at any point around the rotor circumference. The axis is generally viewed to be collinear with shaft 51.

These prior art rotor and centrifuge systems may be used in many different processes involving biological fluid. A method for using the rotor generally includes the steps of introducing an unseparated fluid into the rotor's processing chamber, spinning the rotor so as to separate the fluid into denser and lighter constituents, and applying pressure to the diaphragm's exterior side so as to force fluid components—usually the lighter fluid components—through a conduit out of the chamber.

SUMMARY OF THE INVENTION

In a first embodiment of the invention, there is provided a fluid processing disposable set having a variable-volume chamber and a fluid port, wherein a shaped diaphragm defines a wall of the chamber. The chamber is in fluid communication with the fluid port and is defined by a fixed wall and an elastic wall. The elastic wall is formed by the shaped diaphragm. The disposable set may also have a rotary seal coupled to the fluid port and fluidly coupled to the variable-volume chamber. The shaped diaphragm may be convoluted. The convolution may be a single fold and may have a plurality of folds located symmetrically about an axis. The shaped diaphragm may, alternatively, be essentially planar in an unstretched position while varying in thickness.

In another embodiment, a rotor for use in a centrifuge system is provided. The rotor includes a fixed portion with a conduit assembly and a rigid mounting member that is rotatably mounted around the fixed portion and the axis of rotation of the rotor. The mounting member is capable of being held and spun by a spinning means. Further, the rotor has a shaped diaphragm mounted to the rigid mounting member. The diaphragm is adapted to rotate with the rigid mounting member thereby defining a variable-volume chamber. The rotor may have a rotary seal providing a seal between the rigid mounting member and the fixed portion. Its rigid mounting member may have a boundary wall which, together with the shaped diaphragm, defines the variable-volume chamber. The shaped diaphragm may be convoluted.

Other rotors, systems, and methods for selective harvest of fluid constituents from a whole fluid are provided in further embodiments of the present invention.

DETAILED DESCRIPTION OF SPECIFIC EMBODIMENTS

Figure 7:
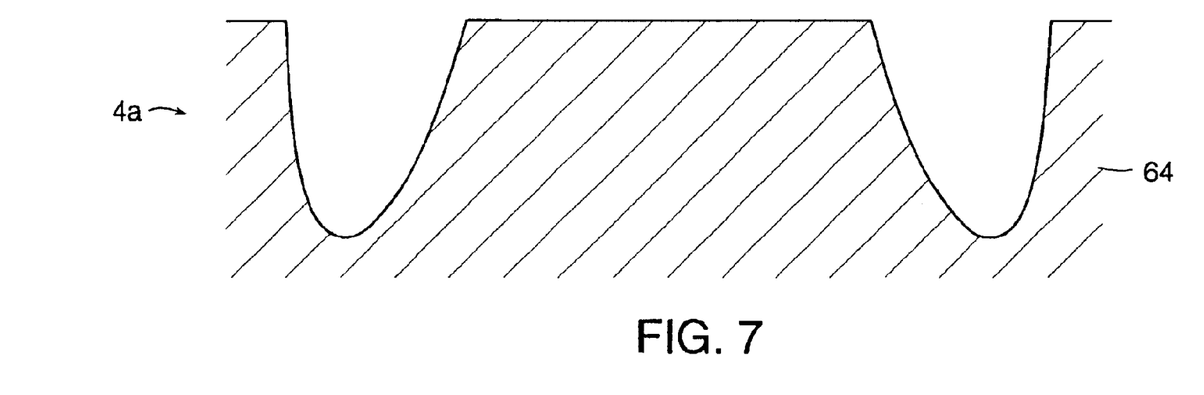
FIGS. 7(a), 7(b), and 7(c) represent exploded views of a simple diaphragm 71 (prior art, 7(a)) and of shaped, essentially planar diaphragms (72, 7(b) and 75, 7(c)) as a part of a disposable set to be used in conjunction with a centrosymmetric chuck, in accordance with an embodiment.
Figure 7A:
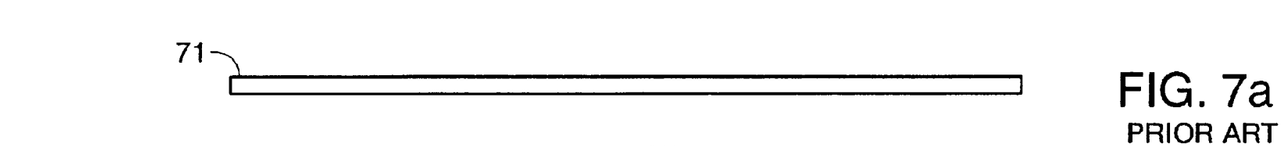
Figure 7B:
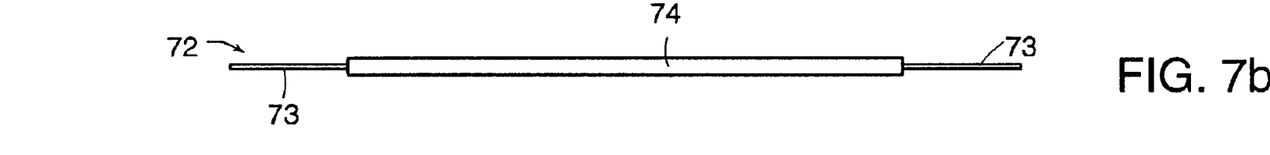
Figure 7C:
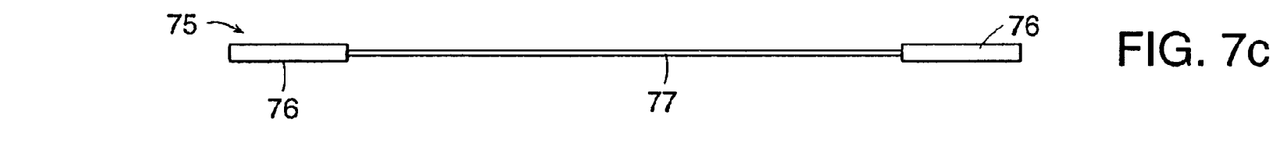

Referring first to FIGS. 7(b) and 7(c), selectively shaped diaphragms such as are denoted therein as reference items 72 and 75 may be used in conjunction with prior art chucks and rotors for fluid centrifugation. Such diaphragms become part of disposable sets for fluid processing applications. Generically, within this specification and the appended claims, the adjective "shaped" is used as a modifier describing any diaphragm having a shape other than that of an essentially planar body and other than having an essentially constant thickness along a dimension when that body is in its lowest energy state (namely, its unstretched position.) An essentially planar diaphragm that has an essentially constant thickness while in its essentially unstretched position (and, in the case of the prior art rotor designs, thereby affording a minimum volume fluid processing chamber) was earlier defined as a "simple" diaphragm. Diaphragm 71 of FIG. 7(a) is such a simple diaphragm. As described earlier, however, simple diaphragm 71 may include a non-planar region in the immediate vicinity of its attachment to/its seal with a wall or another mounting member (i.e. a rim or other such equivalently functional mounting feature). The above definition of "shaped" includes generally planar shapes having intentionally variable thickness along an unstretched length as are shown as items 72 and 75. The "variable thickness" shaped diaphragms are described in the context of their use in providing superior, versatile variable-volume fluid processing chambers in conjunction with a prior art, centrosymmetric chuck 4a with core 64. Fabrication of such molded, shaped membranes is straightforward and may, based upon application-specific stress calculations, provide longer life diaphragms. Shaped diaphragm 72 is molded (or otherwise formed) to be intentionally thicker within its first, more central portion 74 than at outer portions 73. Alternatively, shaped diaphragm 75 is formed intentionally thicker at outer portions 76 than at more central portion 77. Factors which may assist in determining optimal diaphragm shape include number of centrifuge cycles required before breakage (diaphragm life), fluid viscosity, quantity of fluid being processed, and the force required/available to extend the diaphragm into its maximum chamber volume position.

Figure 8:
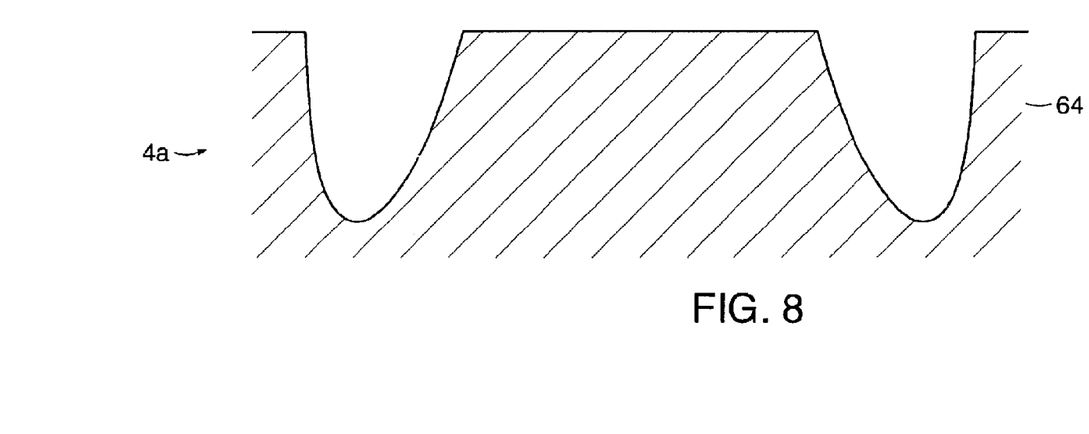
FIGS. 8(a), 8(b), and 8(c) represent exploded views of shaped, convoluted diaphragms 81 (8(a)), 82(8(b)), and 83 (8(c)) as a part of a disposable set to be used in conjunction with a centrosymmetric chuck, in accordance with embodiments.
Figure 8A:
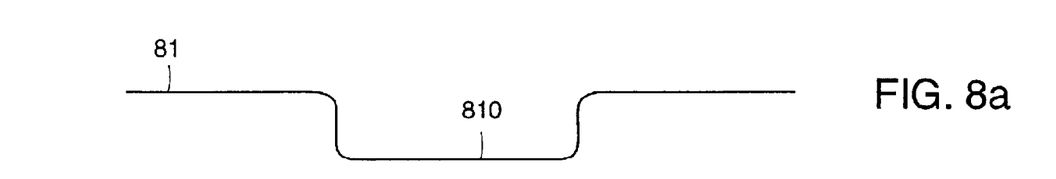
Figures 8B, 8C:
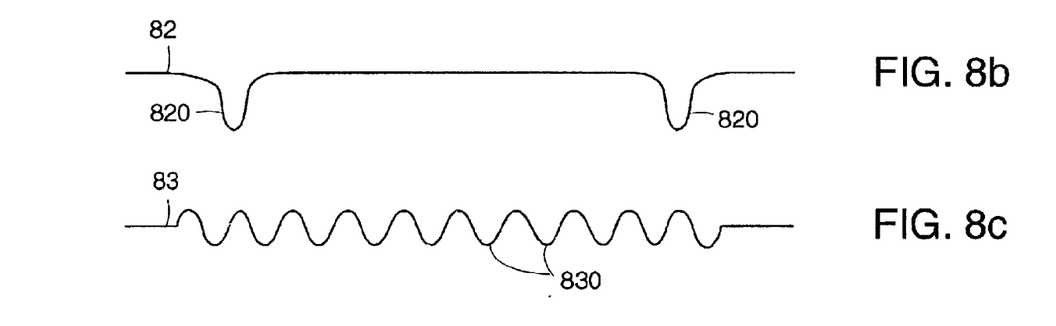

Additional embodiments of selectively shaped diaphragms now to be described exhibit some degree of convolution. By definition, these shapes are not planar when in their essentially unstretched position. These shaped, convoluted diaphragm embodiments may also be formed with intentional thickness variations, although the accompanying figures do not specifically show such embodiments. The diaphragm embodiments of FIGS. 8(a), 8(b), and 8(c) have longer "effective" length, so that when they are distended into core 64 of chuck 4a, the provided slack will afford greater resistance to catastrophic failure. These diaphragm embodiments are shown being used in conjunction with prior art, centrosymmetric chucks. With reference now to FIG. 8(a), shaped, convoluted diaphragm 81 is made with a single fold 810 located in its more central portion. Shaped, convoluted diaphragm 82 is made with a pair of dimples 820, located essentially symmetrically about the axis of rotation (FIG. 8(b)), while shaped diaphragm 83 features periodic undulations 830 which thereby lead to a more substantial "effective" length increase. Similar design factors to those previously described for non-convoluted diaphragms would be useful to find optimal shapes for specific fluid processing applications. It is to be understood that the particular embodiments of shaped, convoluted diaphragms in no way limits the concept and spirit of what is being disclosed herein.

Figure 9A:
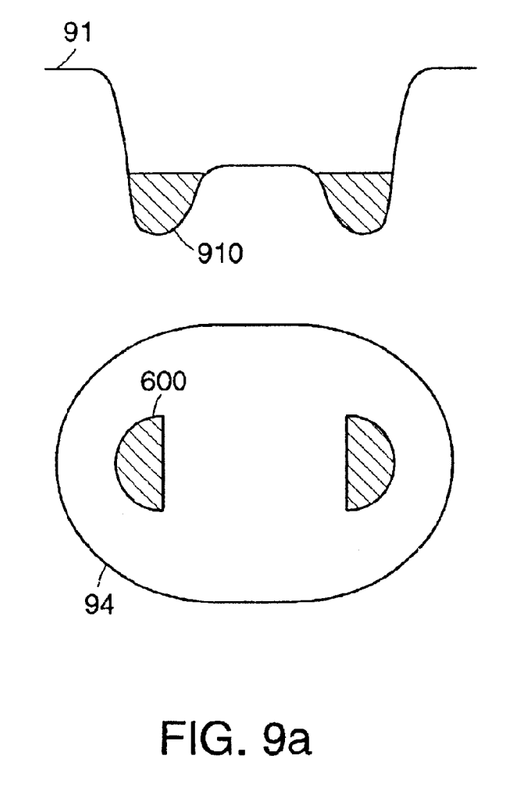
FIGS. 9(a) and 9(b) schematically illustrate embodiments of shaped, convoluted diaphragms with mated centrosymmetric chucks (chucks shown in plan view) for selective fluid capture.
Figure 9B:
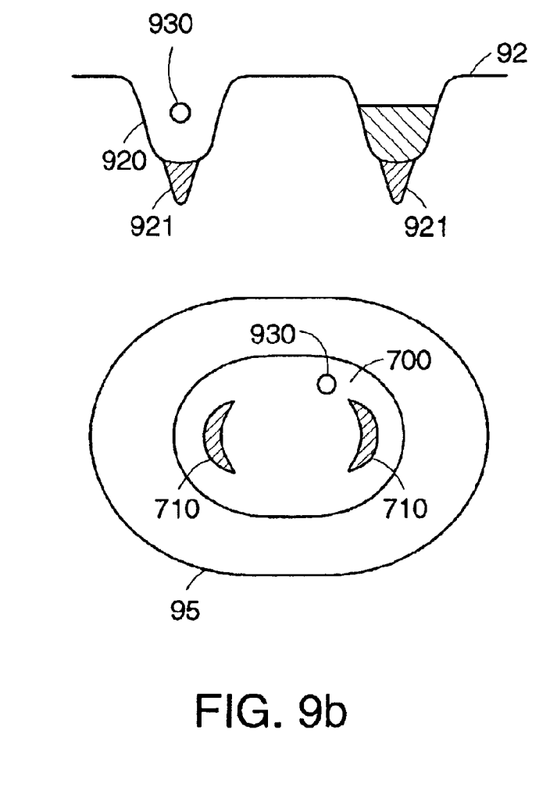

FIGS. 9(a) and 9(b), in accordance with further embodiments, illustrate shaped, convoluted diaphragms and mated centrosymmetric chucks (chucks are shown in plan view) for selective fluid capture. What is different about these chucks is that their core features, into which shaped diaphragms 91 and 92 would distend upon filling and spinning, are discretely, symmetrically indexed around the circumference of the chuck. Shaped diaphragm 91 is formed with a pair of discrete convolutions 910; the first oriented at zero degrees and the second at one-hundred and eighty degrees when viewed along the axis of rotation. Features 600 of chuck 94 are located at each of these two indexed positions to accept convolutions 910 as they are filled with fluid. This arrangement may provide superior harvesting, particularly when the volume of whole fluid to be processed is small. The variation shown in FIG. 9(b) facilitates capture of constituents within the confines of discrete convolutions 920 and, optionally, within discrete pockets 921 formed in shaped diaphragm 92. Other fluid constituents may pass out of the rotor via a second outlet means, namely, groove 930. Features 710 of chuck 95 are, again, located at two discrete, indexed positions to accept convolutions 920 and 921; outlet 700 is mated to accept fluid from a one-dimensional port or a two-dimensional channel 930.

Figure 10A:
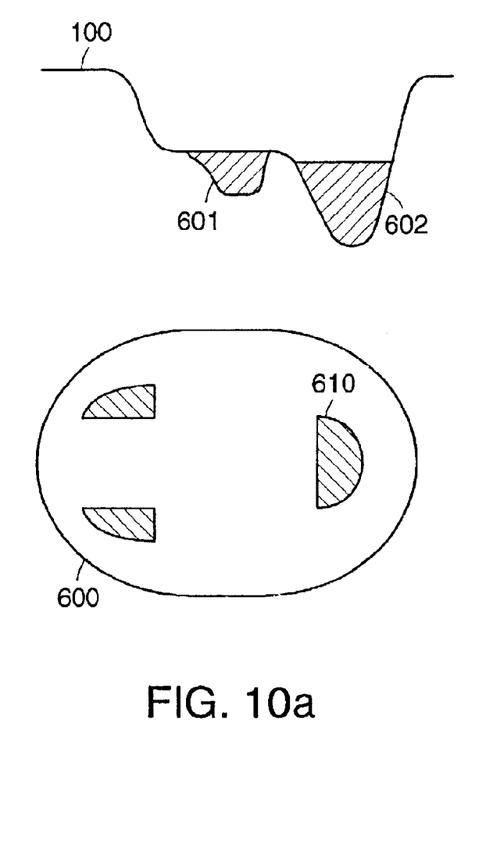
FIGS. 10(a) and 10(b) schematically illustrate embodiments of shaped, convoluted diaphragms with mated asymmetric chucks (chucks shown in plan view) for selective fluid capture.
Figure 10B:
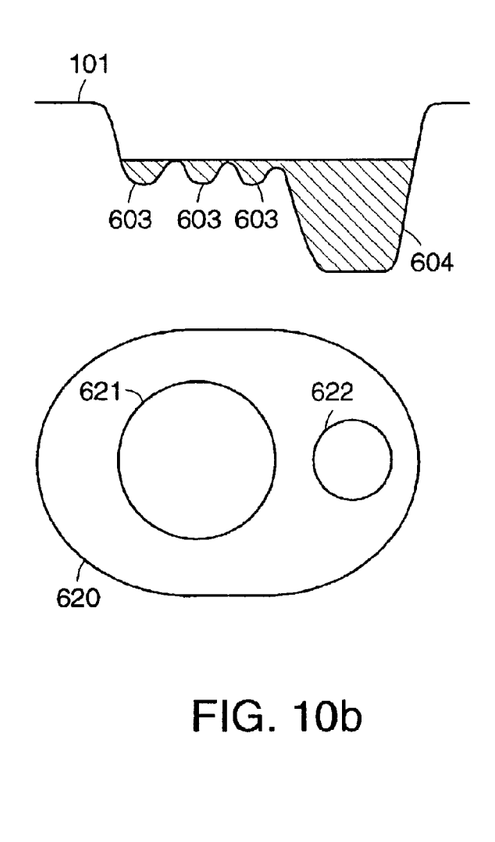

Heretofore, shaped diaphragm embodiments have been described in conjunction with centrosymmetric chucks (i.e. chucks having centrosymmetric features disposed upon their mating surfaces.) In yet other embodiments, illustrated by example in FIGS. 10(a) and 10(b), asymmetrically convoluted diaphragms 100 and 101, are formed with asymmetrically-positioned convolutions 601–604. Diaphragm 100 is shown such that convolution 601 is located essentially on the axis of rotation and is not mated with any core feature 610 of chuck 600. In contrast, convolution 602 may be mated with any of the three illustrated core features 610. Convolutions and core features may be of any shape and dimension to achieve the desired selective harvesting of fluid constituents. The embodiment of FIG. 10(b) first features small, shallow convolutions 603 formed in shaped diaphragm 101 mated to core feature 621 located on a first half of the surface of chuck 620. Second, it features a larger convolution 604 formed in shaped diaphragm 101 mated to core feature 622 located on a second half of the surface of chuck 620. These more intricate embodiments reveal the numerous possible design configurations possible when shaped diaphragms are used in centrifuge rotors. The nature of the fluid constituents as well as those particularly of interest for harvesting will impact configuration selection.

Although the invention has been described with reference to several preferred embodiments, it will be understood by one of ordinary skill in the art that various modifications can be made without departing from the spirit and the scope of the invention, as set forth in the claims hereinbelow.

We claim:

1. A fluid processing disposable set comprising:
   a fluid port;
   a variable-volume chamber in fluid communication with the fluid port, the chamber defined by a rigid wall and an elastic wall; and
   a rigid bottom surface spanning the variable-volume chamber, limiting the upward movement of the elastic wall and comprising an interior wall located within the chamber, the rigid bottom surface being substantially flat across the chamber, and the interior wall having at least one hole for permitting the passage of fluid therethrough;
   the elastic wall formed by a convoluted diaphragm with a region of convolution, the region of convolution separated from the center of the elastic wall by a region without convolution, such that the region without convolution is substantially adjacent to the substantially flat rigid bottom surface when in an unstretched state.

2. A fluid processing disposable set according to claim 1 further comprising:
   a rotary seal coupled to the fluid port, the rotary seal fluidly coupled to the chamber.

3. A fluid processing disposable set according to claim 1, wherein the convoluted diaphragm has at least one fold.

4. A fluid processing disposable set according to claim 3, wherein the convoluted diaphragm has a plurality of folds, the folds located symmetrically about an axis.

5. A fluid processing disposable set according to claim 1, wherein the rigid bottom surface further comprises a portion of the rigid wall.

6. A fluid processing disposable set according to claim 5, further including a groove within the rigid bottom surface permitting passage of fluid through the groove to the hole.

7. A fluid processing disposable set according to claim 1, further including a discrete pocket within the convolution.

8. A fluid processing disposable set according to claim 7, wherein the discrete pocket may be accepted by a feature in a chuck.

9. A fluid processing disposable set according to claim 1, further including a groove within the rigid bottom surface permitting passage of fluid through the groove to the hole.

10. A fluid processing disposable set comprising:
    a fluid port;
    a variable-volume chamber in fluid communication with the fluid port, the chamber defined by a rigid wall and an elastic wall, the elastic wall sealed only at a mounting position on the rigid wall and formed by a shaped diaphragm; and
    a rotary seal coupled to the fluid port, the rotary seal fluidly coupled to the chamber, wherein the shaped diaphragm is essentially planar in an unstretched position, the diaphragm varying in thickness so as to have a local maximum in thickness outside the mounting position's immediate vicinity.

11. A fluid processing disposable set according to claim 10, wherein the thickness is constant at locations equidistant from an axis.

12. A fluid processing disposable set according to claim 10, further including a rigid bottom surface limiting, at least in part, the upward movement of the elastic wall.

13. A fluid processing disposable set according to claim 12, wherein the rigid bottom surface is substantially flat.

14. A fluid processing disposable set according to claim 13, further including an interior wall located within the chamber and forming a part of the rigid bottom surface.

15. A fluid processing disposable set according to claim 14, further including at least one hole within the interior wall for permitting the passage of fluid therethrough.

16. A fluid processing disposable set according to claim 15, further including a groove within the rigid bottom surface permitting passage of fluid through the groove to the hole.

17. A fluid processing disposable set comprising:
    a fluid port;
    a variable-volume chamber in fluid communication with the fluid port, the chamber defined by a rigid wall and an elastic wall; and
    a rigid bottom surface spanning the variable-volume chamber, limiting the upward movement of the elastic wall and comprising an interior wall located within the chamber, the rigid bottom surface being substantially planar across the chamber, and the interior wall having at least one hole for permitting the passage of fluid therethrough;
    the elastic wall formed by a diaphragm with at least one convolution, the convolution being a contiguous region of the diaphragm where the diaphragm in an unstretched state departs from the plane of the rigid bottom surface.

18. The fluid processing disposable set of claim 17, wherein the convolution is symmetrically disposed about an axis of rotation of the diaphragm.

19. The fluid processing disposable set of claim 18, wherein the convolution is distendable into a core.

20. The fluid processing disposable set of claim 17, wherein the convolution is exclusive of an axis of rotation of the diaphragm.

21. The fluid processing disposable set of claim 20, wherein the convolution is distendable into a core.

22. The fluid processing disposable set of claim 20, further including a plurality of convolutions.

23. The fluid processing disposable set of claim 22, wherein, the convolutions are discrete and are symmetrically positioned about an axis of rotation of a chuck, and distendable into core features of the chuck.

24. The fluid processing disposable set of claim 22, wherein, the convolutions are discrete and are asymmetrically positioned about an axis of rotation of a chuck, and distendable into core features of the chuck.

* * * * *